United States Patent
Smith et al.

(10) Patent No.: US 9,308,128 B2
(45) Date of Patent: Apr. 12, 2016

(54) MULTI-SPOT LASER PROBE WITH MICRO-STRUCTURED FACETED PROXIMAL SURFACE

(71) Applicant: Novartis AG, Basel (CH)

(72) Inventors: Ronald T. Smith, Irvine, CA (US); Mark H. Farley, Laguna Hills, CA (US); Dustin J. Bouch, Petaluma, CA (US)

(73) Assignee: NOVARTIS AG, Basel (CH)

( * ) Notice: Subject to any disclaimer, the term of this patent is extended or adjusted under 35 U.S.C. 154(b) by 406 days.

(21) Appl. No.: 13/736,506

(22) Filed: Jan. 8, 2013

(65) Prior Publication Data

US 2014/0194862 A1 Jul. 10, 2014

(51) Int. Cl.
*A61B 18/22* (2006.01)
*A61F 9/008* (2006.01)

(52) U.S. Cl.
CPC ... *A61F 9/00821* (2013.01); *A61F 2009/00863* (2013.01)

(58) Field of Classification Search
CPC ............... A61B 2018/2272; A61B 2018/2277; G02B 3/0056; G02B 3/08; G02B 6/3861
USPC .................... 606/2–19; 607/88, 89
See application file for complete search history.

(56) References Cited

U.S. PATENT DOCUMENTS

| | | | |
|---|---|---|---|
| 4,209,017 A | 6/1980 | Shaw | |
| 4,669,818 A | 6/1987 | Myer | |
| 5,451,221 A | 9/1995 | Cho et al. | |
| 5,630,788 A | 5/1997 | Forkner et al. | |
| 6,011,889 A | 1/2000 | Daniel et al. | |
| 6,096,028 A | 8/2000 | Bahmanyar et al. | |
| 7,027,478 B2 | 4/2006 | Ackley | |
| 2005/0243570 A1 | 11/2005 | Chaves et al. | |
| 2006/0263034 A1 | 11/2006 | Sakurai et al. | |
| 2007/0121069 A1 | 5/2007 | Andersen et al. | |
| 2008/0086160 A1 | 4/2008 | Mastri et al. | |
| 2008/0108981 A1 | 5/2008 | Teifair et al. | |

(Continued)

FOREIGN PATENT DOCUMENTS

| | | |
|---|---|---|
| EP | 0938871 | 9/1999 |
| RU | 2510720 C2 | 4/2014 |
| WO | 2008/045316 | 4/2008 |

OTHER PUBLICATIONS

International Search Report and Written Opinion issued for PCT/US2013/077983 dated May 6, 2014, 9 pgs.

*Primary Examiner* — Aaron Roane
(74) *Attorney, Agent, or Firm* — Haynes and Boone, LLP

(57) ABSTRACT

An optical surgical probe includes a cannula; a light guide within the cannula, configured to receive a light beam from the light source, to guide the light beam to a distal end of the light guide, and to emit the light beam at the distal end of the light guide; and a multi-spot generator at a distal end of the cannula, the multi-spot generator having a faceted proximal surface with oblique facets, configured to receive the light beam emitted at the distal end of the light guide and to split the received light beam into multiple beam-components, and a distal surface through which the multiple beam-components exit the multi-spot generator, wherein the proximal surface of the multi-spot generator is micro-structured with a modulation length smaller than a wavelength of the light beam in order to reduce the reflectance of light back into the probe.

8 Claims, 17 Drawing Sheets

(56) References Cited

U.S. PATENT DOCUMENTS

| | | |
|---|---|---|
| 2009/0190883 A1 | 7/2009 | Kato et al. |
| 2010/0049019 A1 | 2/2010 | Veeck et al. |
| 2011/0122366 A1 | 5/2011 | Smith |
| 2011/0141759 A1 | 6/2011 | Smith |
| 2011/0144627 A1 | 6/2011 | Smith |
| 2013/0038836 A1 | 2/2013 | Smith |
| 2014/0200566 A1 | 7/2014 | Smith |
| 2014/0250668 A1 | 9/2014 | Smith |

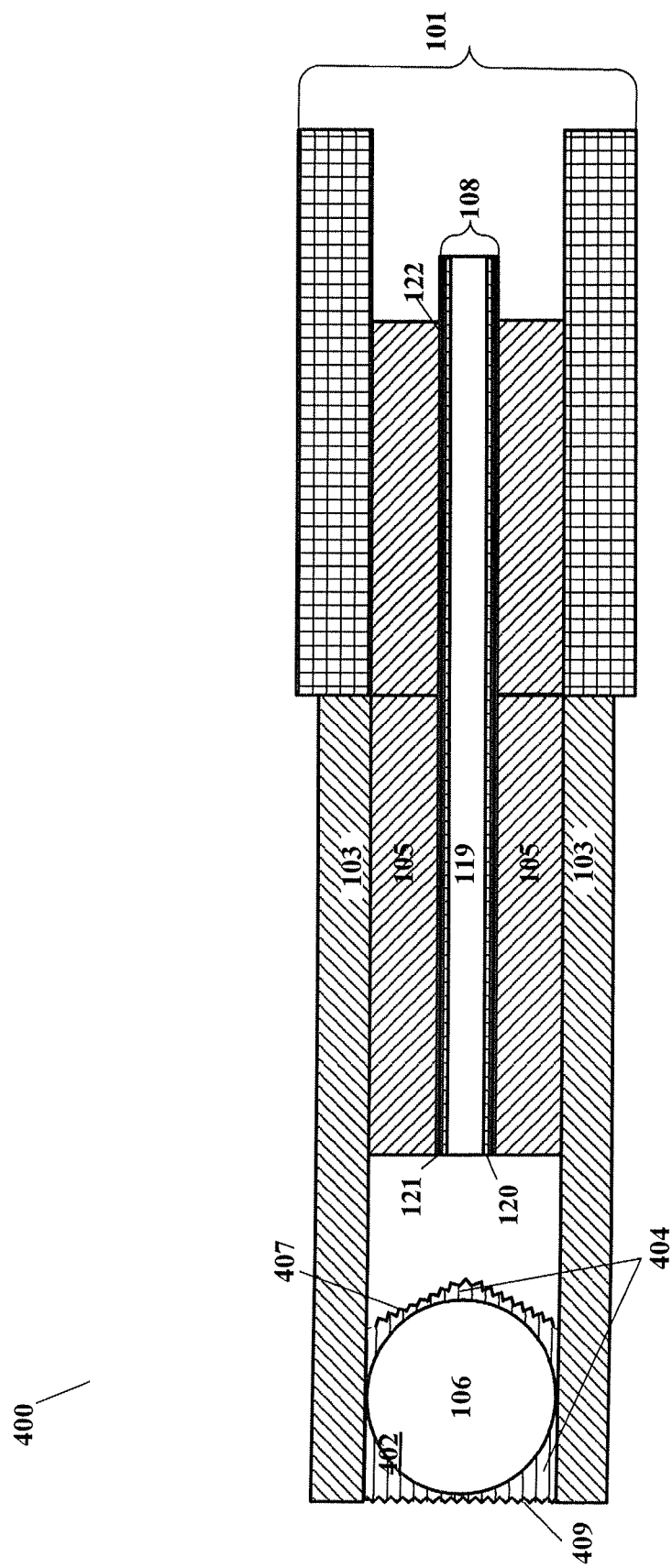

MULTI-SPOT LASER PROBE WITH MICRO-STRUCTURED FACETED PROXIMAL SURFACE

BACKGROUND

1. Technical Field

Embodiments disclosed herein are related to a multi-spot laser probe having a micro-structured faceted proximal surface and methods for manufacturing the same. In particular, some embodiments disclosed herein provide a multi-spot laser probe having a micro-structured faceted proximal surface and a micro-structured distal surface and method for manufacturing the same that may reduce a total internal reflectance back into the laser probe.

2. Related Art

Laser probes may deliver light to multiple spots onto a surgical target. For example, in the course of pan-retinal photocoagulation of retinal tissue, delivering light to multiple spots can reduce the time of the surgical procedure. In existing system various techniques have been employed to produce multiple beams for a multi-spot pattern. For example, one approach uses diffractive elements at the distal end of the probe to divide an incoming beam into multiple beams.

Difficulties, however, can arise with using diffractive elements at the distal end of the probe. For example, diffractive elements can produce a multitude of higher diffraction orders and thus a large number of additional, unwanted, extraneous beam spots that will irradiate the retina. These additional spots, in spite of having lower intensities, may have negative effects, such as undesirable heating of the target region. Moreover, a diffractive element may not perform the same in different refractive media. For example, a diffractive element may be placed into a medium with a different refractive index than that of air, and spaces between the diffractive elements may fill with the medium, which may affect the spot pattern. Furthermore, the spacing between the spots can vary for different wavelengths, which can cause problems if an aiming beam and a treatment beam are different colors. Diffractive elements are also frequently expensive and difficult to produce, especially if the diffractive element is to fit into a small area.

Some laser probes utilize a single fiber to guide the light from a light source to a ball lens. The ball lens can be immersed into a cured, optically transmissive adhesive with multiple facets to split the light beam. However, both the proximal and the distal surfaces of the cured adhesive reflect as much as 5% of the incident light back into the laser probe, causing problems related to overheating such as material degradation of the adhesive.

Accordingly, there is a need for a multi-spot laser probe that (a) can provide multiple spots at a surgical target without overheating the probe, (b) without the problems associated with diffractive elements, and (c) that can be fabricated at an acceptable cost.

SUMMARY

Consistent with some embodiments, there is provided an optical surgical probe that includes a cylindrical cannula; a light guide within the cannula, configured to receive a light beam from the light source, to guide the light beam to a distal end of the light guide, and to emit the light beam at the distal end of the light guide; and a multi-spot generator at a distal end of the cannula, the multi-spot generator having a faceted proximal surface with oblique facets, configured to receive the light beam emitted at the distal end of the light guide and to split the received light beam into multiple beam-components, and a distal surface from which the multiple beam components exit the multi-spot generator, wherein the proximal surface of the multi-spot generator is micro-structured with a modulation length smaller than a wavelength of the light beam.

Consistent with some embodiments, a method for manufacturing a multi-spot generator for an optical surgical probe can include depositing an optically transmissive adhesive medium on the surface of the substrate with an applicator; inserting an optical element into the adhesive medium; placing a pin with an obliquely faceted and micro-structured distal end onto the adhesive medium to form an obliquely faceted micro-structured proximal surface on the adhesive medium, thus forming a pin-adhesive-optical element-substrate assembly; placing a cannula onto the pin-adhesive-optical element-substrate assembly to house the multi-spot generator within the cannula; curing the adhesive medium; and separating the substrate and the pin from the multi-spot generator housed within the cannula.

BRIEF DESCRIPTION OF THE DRAWINGS

FIG. 4 is a diagram illustrating the distal end of a multi-spot laser probe with a multi-spot generator having a micro-structured distal surface and a micro-structured faceted proximal surface.

Figure 1:
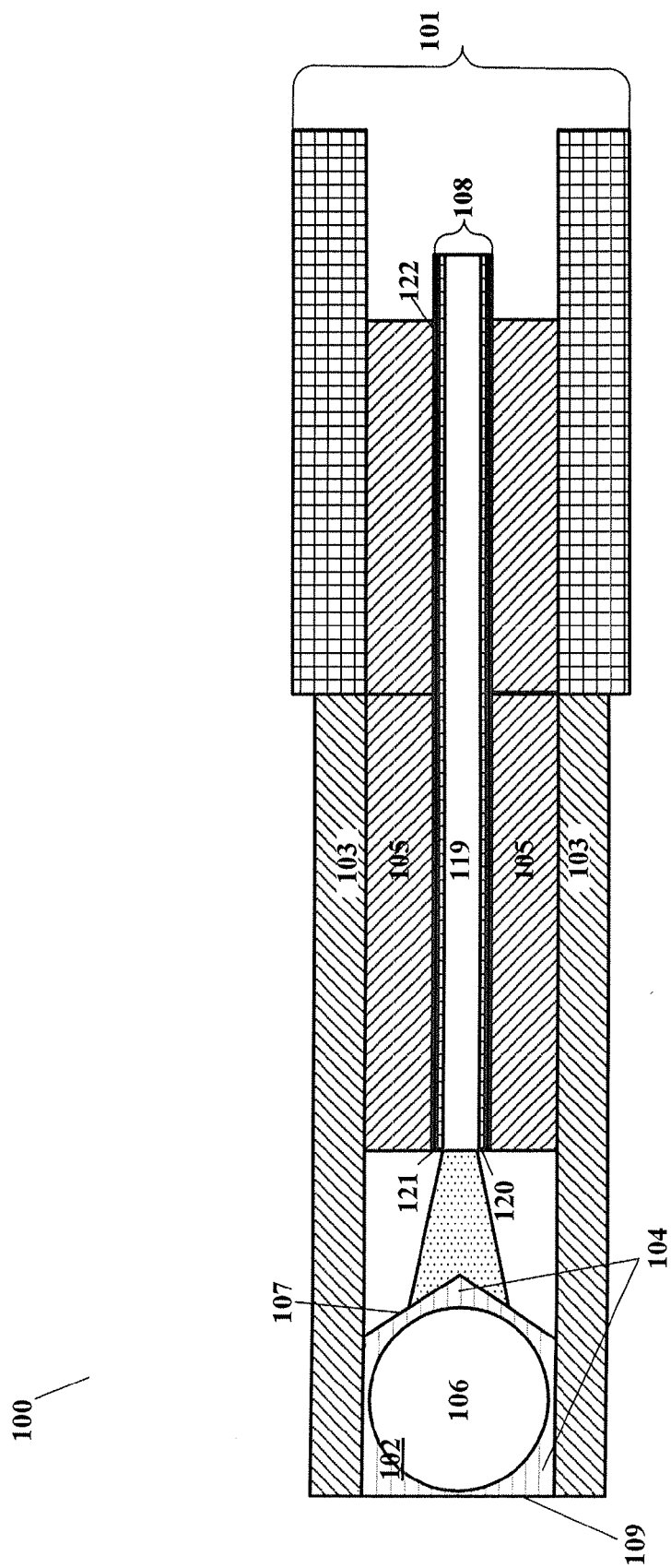
FIG. 1 is a diagram illustrating a multi-spot laser probe.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

FIG. 1 illustrates an example of an optical surgical probe 100 that includes a cylindrical cannula 103, and a light guide 108 within the cannula 103, configured to receive a light beam from the light source, to guide the light beam to a distal end of the light guide 108, and to emit the light beam at the distal surface of the light guide 108. The light guide 108 can be an optical fiber, disposed within a stainless steel ferrule 105. The optical surgical probe 100 can further include a multi-spot generator 102 housed within a distal end of the cannula 103. The multi-spot generator 102 can have a faceted proximal surface 107 with oblique facets, configured to receive the light beam emitted at the distal end of the light guide 108 and to split the received light beam into multiple beam-components.

As used throughout this disclosure, "proximal" refers to a surface or region of an object closest to the light source along a path of the laser beam, and "distal" refers to a surface or region of the object farthest from the light source, and thus closest to the target.

Consistent with some embodiments, the optical surgical probe 100 can include a cannula housing 101, to be abutted to the cannula 103 and to surround the ferrule 105. The optical fiber 108 may be any suitable structure for transmitting light. In some embodiments, the optical fiber 108 may include a core 119, a cladding 120, and a jacket 121. The optical fiber 108 can be affixed to the ferrule 105 with an adhesive 122. Any suitable size optical fiber 108 may be used, e.g., the core 119 may have a diameter in the range of 75 to 150 microns. A larger diameter for the core 119 generally yields a larger spot.

The cannula 103 can house the multi-spot generator 102 and the ferrule 105 that can in turn accommodate the optical fiber 108. Both the cannula 103 and the ferrule 105 may be configured to fit together to align the optical fiber 108 and the multi-spot generator 102. "Alignment" may be defined in any suitable manner. For example, two parts can be aligned if the rotational axis of one part substantially coincides with the rotational axis of the other part. As another example, two parts can be aligned if substantially all of a laser beam transmitted by one part is received by the other part.

The multi-spot generator 102 can include a cured optically transmissive adhesive medium 104 and a ball lens 106 disposed in the adhesive medium 104. The adhesive medium 104 can have a faceted proximal surface 107.

Consistent with some embodiments, the faceted proximal surface 107 of the multi-spot generator 102 can be configured to split the incident laser beam into multiple beam-components that can produce multiple laser spots at a target. Such a beam will be termed a multi-spot beam. In one example, a somewhat divergent laser beam can be emitted by the optical fiber 108. Portions of the divergent laser beam can fall on the different facets of the faceted proximal surface 107. Each facet of the faceted proximal surface 107 can refract its incident beam portion into a different direction to yield a beam-component of the multi-spot beam. The beam-components can be transmitted and focused by the ball lens 106. The beam-components can exit the optical laser probe 100 through a planar distal surface 109 of the adhesive medium 104.

As the beam is scanned or moved during surgery, the distance between the distal end of the optical surgical probe 100 and the target surface can vary or change. This variation may modify the spot diameters and spot separations, and in general the spot pattern, making it less regular. Thus, designing the faceted proximal surface 107 and the ball lens 106 to focus the multi-spot beam onto a relatively distant target enables the size of the beam spots and the general divergence of the multi-spot beam to be minimized.

The faceted proximal surface 107 may have any suitable number and shape of facets. In certain embodiments, the faceted proximal surface 107 may have N facets oblique to the beam path that meet at a point aligned with a center of the laser beam from the optical fiber 108 such that the multi-spot generator 102 produces N beam-components of similar characteristics, where N=3, 4, 5, or another suitable integer. In other embodiments, the faceted proximal surface 107 may have a central planar facet perpendicular to the beam path with N surrounding obliquely-angled facets to produce a central spot surrounded by N spots. Any suitable slant angle between the facets may be used. The optimal angle can be determined by the index of refraction of the adhesive medium 104 and can be 20°-30° degrees, such as 27° degrees. In general, decreasing the slant angle may decrease the separation between the spots. Consistent with some embodiments, at least one facet is oriented oblique to the beam path, such that a direction normal to a facet at a center of the facet is not parallel to the beam path of the laser beam.

The ball lens 106 can be an optical element that refracts an incident beam or beam-components to emerge at the distal surface 109 of the multi-spot generator 102 collimated or with a small angle of divergence or convergence. In some embodiments the ball lens 106 can slightly converge the multi-spot beam in order to focus the beam spot pattern onto a relatively distant target, such as the retina. Consistent with some embodiments, the ball lens 106 can be a sapphire ball. The ball lens 106 may have a variety of analogous shapes, such as a sphere, an approximate sphere, or a portion of a sphere (e.g., a hemisphere). The ball lens 106 may comprise any refractive material.

In certain embodiments, the ball lens 106 and the adhesive medium 104 can have different refractive indices. To focus a collimated or converging beam, the refractive index of the ball lens 106 should be greater than that of the adhesive medium 104. For example, the ball lens 106 may be a sapphire ball lens with a visible refractive index of about 1.76, whereas the adhesive medium 104 may have a lower adhesive refractive index in the range of 1.56-1.58.

In other embodiments, faceted proximal surface 107 can be obliquely concave. The ball lens 106 may still be able to converge the beam-components created by the concave facets to produce a multi-spot pattern.

Figure 2:
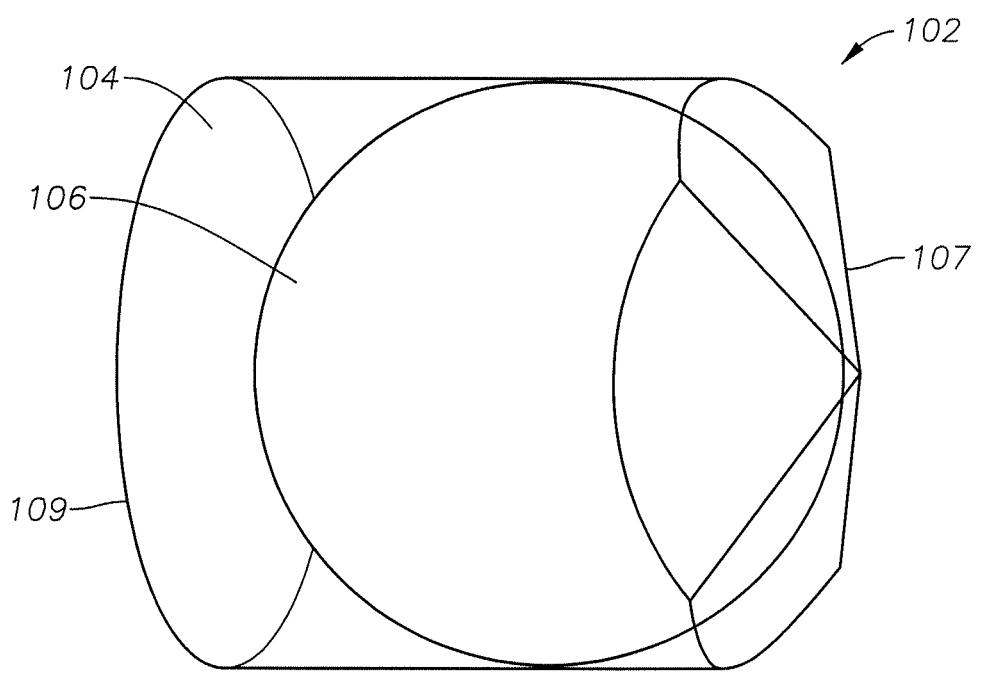
FIG. 2 is a diagram illustrating a multi-spot generator.

FIG. 2 is a diagram illustrating the multi-spot generator 102, consistent with some embodiments. As shown in FIG. 2, the multi-spot generator 102 can include the ball lens 106 encased in the adhesive medium 104, wherein the adhesive medium 104 can have the faceted proximal surface 107. Consistent with some embodiments, the adhesive medium 104 can have a refractive index in the range of 1.5-1.6, or in some cases 1.56-1.58. The adhesive medium 104 can be curable by ultraviolet light to provide mechanical and material stability and precise dimensional control. The faceted proximal surface 107 may be obliquely convex with a degree of tilt of 20°-30°, such as 27°. Consistent with some embodiments, the multi-spot generator 102 may be formed by encasing the ball lens 106 in the adhesive medium 104, and then forming the faceted proximal surface 107 on a proximal end of the adhesive medium 104.

Figure 3A:
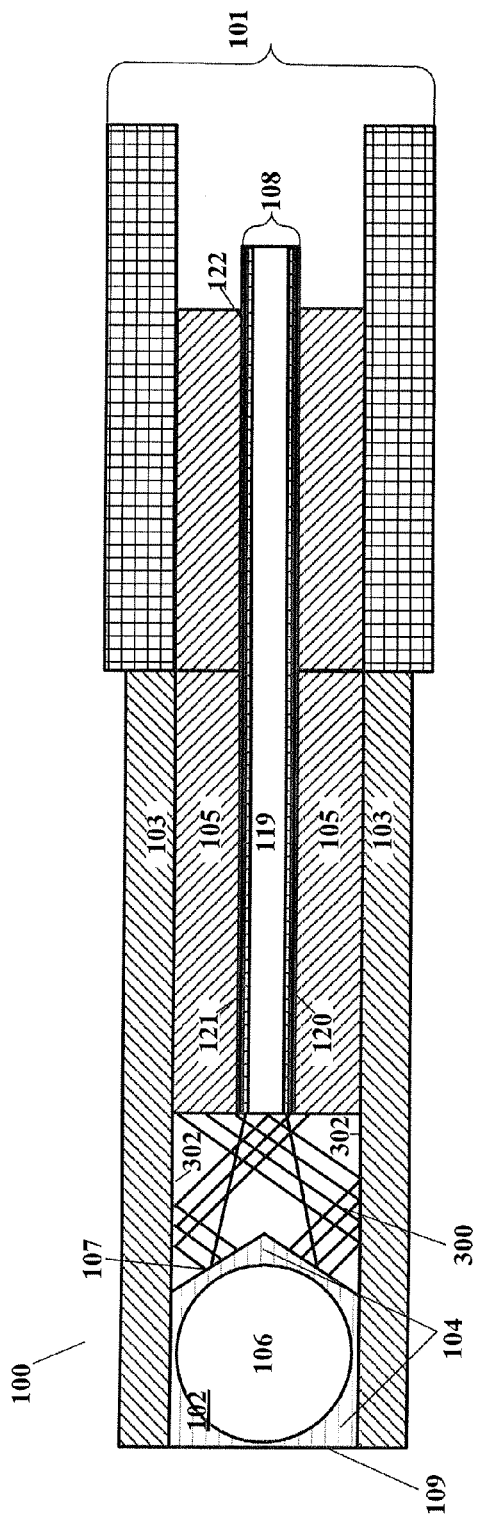
FIGS. 3A-B are diagrams illustrating the reflection of light within the distal end of the multi-spot laser probe.
Figure 3B:
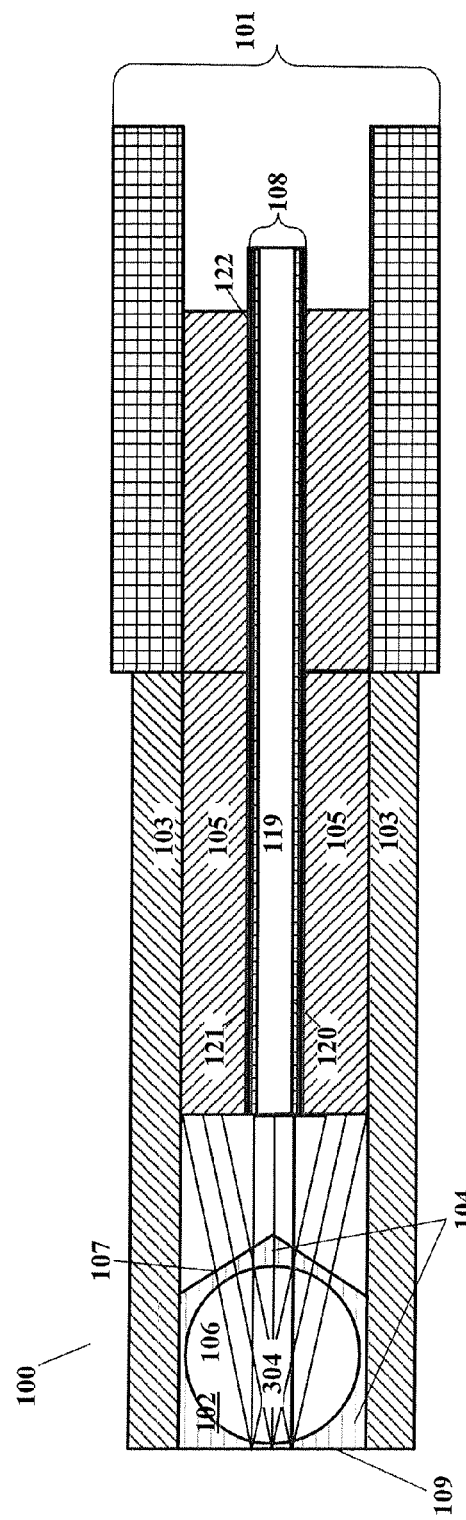

FIGS. 3A-B illustrate that, as discussed earlier, in some existing multi-spot generators 102 the Fresnel reflectance of laser light off of the proximal surface 107 and the distal surface 109 of the adhesive medium 104 can reflect a substantial portion of the laser light back into the optical surgical probe 100, causing the probe tip to disadvantageously heat up. As shown in FIG. 3A, light emitted from the distal end of the light guide 108 can undergo a Fresnel reflection at the proximal surface 107 of the adhesive medium 104, generating a reflected beam 300. In some cases, the intensity of the reflected beam 300 can be as high as about 5% of the light that irradiates the faceted proximal surface 107. The reflected beam 300 can then be partially incident on interior surfaces 302 of the cannula 103, wherein about 30-40% of its power can be reflected again, possibly being redirected to the ferrule 105 and light guide 108, and 60-70% of the beam's power can be absorbed by the interior surfaces 302 of the cannula 103.

FIG. 3B illustrates that the light that travels through the faceted proximal surface 107 un-reflected can undergo a Fresnel reflection at a distal planar surface 109 of the optical surgical probe 100 and generate a reflected beam 304 which is transmitted back into the optical surgical probe 100. There again, the reflected beam 304 can be absorbed by the interior surfaces 302 of the cannula 103 and the ferrule 105. In some cases, the intensity of the reflected beam 304 can be as high as 5% of the intensity of the light that travels through the ball lens 106. Accordingly, reflected beams 300 and 304 together can cause up to about 10% of the incident laser light emitted by the optical fiber or light guide 108 to be reflected back into the tip of the optical surgical probe 100, increasing its temperature.

The elevated temperature may reduce the performance of the optical surgical probe 100 in various ways. For example, in some case, the temperature of the adhesive medium 104 may be elevated to the point that it becomes fluid, letting the ball lens 106 to become loose and move or rotate away from its optimal position and orientation. In a worst case scenario, the ball lens 106 may even fall from the cannula 103, possibly into the interior of the eye, a highly undesirable outcome. In some other cases, the material of the adhesive medium 104 may thermally degrade and become less transparent, or have its optical performance reduced in some other way.

An improvement could be to deposit or form an anti-reflection (AR) coating on the proximal surface 107. Further improvements can be also achieved by depositing an anti-reflection (AR) coating on the distal surface 109 as well. The AR coating can be made of one or more dielectric layers having well-defined refractive indices, thicknesses, and surface characteristics to suppress the Fresnel reflectance at the proximal and distal surfaces of the adhesive medium and thus the intensity of the reflected beams 300 and 304. However, forming and depositing the dielectric AR coating on the adhesive medium 104 requires a high deposition temperature which may deform the adhesive medium 104 or change its optical properties. Moreover, material incompatibilities between the AR coating and the adhesive medium 104 may make it difficult for the AR coating to adhere to the adhesive medium 104. For all these reasons, designs which use AR coating to reduce heating have substantial drawbacks.

FIG. 4 is a diagram illustrating an optical surgical probe 400 with a multi-spot generator 402 that reduces heating and thermal effects without a deposited AR coating layer, thus avoiding the previously discussed problems. The optical surgical probe 400 can include elements analogous to those of the optical surgical probe 100, including the cannula housing 101, the cannula 103, the ferrule 105, the ball lens 106, and the light guide or fiber 108. The cannula housing 101 can be encased by a handpiece, configured to be held manually by an operating surgeon. The handpiece can be a plastic or metal cylindrical structure, surrounding the cannula housing 101.

In addition, the optical surgical probe 400 can include the multi-spot generator 402 with a micro-structured faceted proximal surface 407 of an optically transmissive adhesive medium 404. The facets of the micro-structured faceted proximal surface 407 can still be configured to refract portions of the incident light emitted from the optical fiber 108 into different directions to generate beam-components of a multi-spot beam. The ball lens 106 can transmit the beam-components to emit them as the multi-spot beam through a distal surface 409 of the adhesive medium 404.

Consistent with some embodiments, the micro-structured faceted proximal surface 407 may have a moth's eye structure to reduce the reflection of the incident laser beam. A moth's eye structure is so-called because it resembles the tiny surface relief undulations or bumps found on a surface of an eye of a moth or fly. This eye structure reduces the reflection of light off the surface of the eye, making it more difficult for predators to spot the moth.

Consistent with some embodiments, undulations or bumps of the micro-structured surface 407 can be smaller than a multiple of the wavelength of the incoming light to reduce the reflection of light. The multiple can be 3, 1 or 0.3. Expressed differently, a modulation length of the micro-structured faceted proximal surface 407 can be less than 3, 1, or 0.3 times the wavelength of the incoming light. In yet other terms, the micro-structures of the micro-structured surface 407 can have an average separation less than 3, 1 or 0.3 times the wavelength of the light or laser beam. It is noted that the anti-reflective properties of the micro-structured surface 407 improve with decreasing modulation length and decreasing size of the undulations and bumps. In other words, the smaller the just-mentioned multiple, the smaller the reflected portion of the incoming light.

FIG. 4 also shows that, analogously, in some embodiments, the distal surface 409 of the adhesive medium 404 can be micro-structured. The average feature size or modulation length of the micro-structured distal surface 409 can be again less than 3, 1 or 0.3 times the wavelength of light, similarly to the micro-structured proximal surface 407.

Figure 5A:
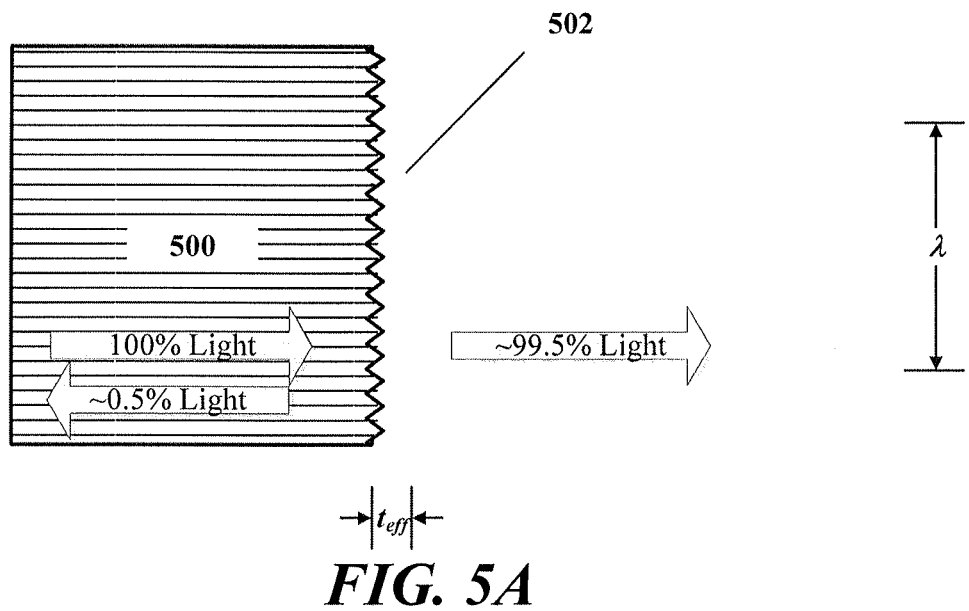
FIGS. 5A-B are diagrams illustrating the reflectance of a micro-structured surface as an effective medium.
Figure 5B:
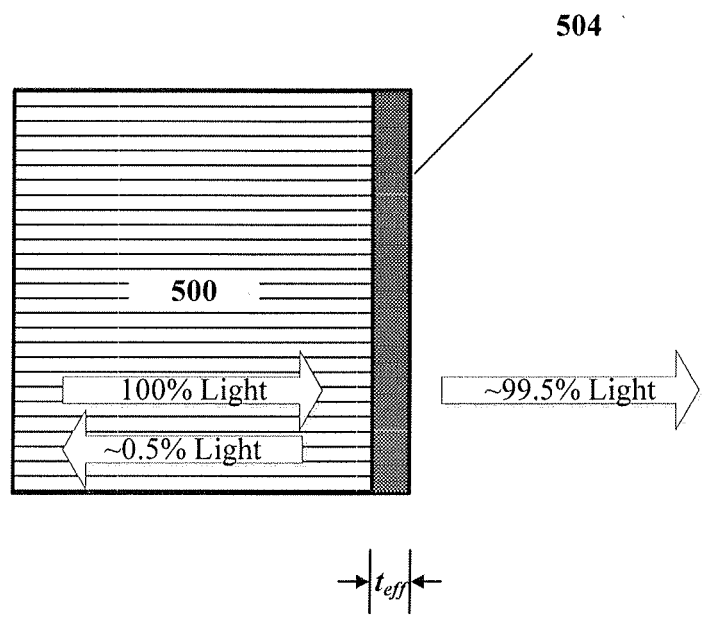

FIGS. 5A-B illustrate how the micro-structures or micro-features of the micro-structured surface 407 reduce the reflectance of the faceted proximal surface 407. The illustration refers to a generic optical medium 500 that can be the adhesive medium 404 and a generic micro-structured surface 502 that can be either the micro-structured faceted proximal surface 407 or the micro-structured distal surface 409.

As is well known from the theory of propagation of electromagnetic waves, when the average size of individual bumps of the micro-structured surface 502 is comparable or larger than $\lambda$, the wavelength of incident light, then the light passing through the surface 502 either diffracts into multiple discrete directions if the micro-structure is periodically repeating, or leaves the surface in a diffuse manner, distributed continuously to all spatial angles if the micro-structure is randomly distributed.

On the other hand, when the average size of the bumps, or the scale of the modulation is small compared to the wavelength $\lambda$ of the incident light then the light "averages out" the micro-structure of the surface 502, and only experiences the traversing the surface 502 as traversing an effective medium 504 of width $t_{eff}$, the typical size of the bumps or micro-features of the micro-structured surface 502. The effective medium 504 can be thought of as an effectively homogenous slab with an effective refractive index $n_{eff}$ that is a weighted average of a refractive index $n_{med}$ of the medium 500 and a refractive index $n_{ambient}$ of the ambient medium. If the external side of the micro-structured surface 502 is surrounded by air, then $n_{ambient}=n_{air}$. If on the external side of the micro-structured surface 502 the ambient medium is not air, but e.g. that of a protective overlayer, a transparent substrate, an embedding material, or an optically refractive target material or biological material, then $n_{ambient}$ is the refractive index of that ambient material or medium. The type of weighting the average for $n_{eff}$ may depend on how and to what degree the bumps fill out the volume of the micro-structured surface 502, depending on the shapes of the bumps of the micro-structured surface 502. The micro-structure can include bumps, cones, prisms, pyramids, grooves, troughs, divots and a relief pattern, each defining its own average refractive averaging.

The design of the micro-structured surface 502 can include selecting a specific effective thickness $t_{eff}$ and a type or shape of the micro-structures or micro-features, such as bumps, pyramids, grooves or other types. These design choices determine the effective refractive index $n_{eff}$ of the micro-structured surface 502. If the effective parameters and their combination, the optical path length $n_{eff}*t_{eff}$ satisfy the condition for destructive interference: $n_{eff}*t_{eff}=\lambda/4$ then the micro-structured surface 502 can exhibit anti-reflective properties similar to a traditional AR coating. Embodiments of the micro-structured surface 502 may be manufactured to have a $t_{eff}$ and exhibit an $n_{eff}$ that combine for a highly efficient transmittance of light at the interface of the optical medium 500 and air/ambient. Specific embodiments can reach a transmittance above 99%, in some cases above 99.5%, and a Fresnel reflectance of less than 1%, in some cases less than 0.5%. One of these embodiments is shown in FIG. 5B.

Figure 6:
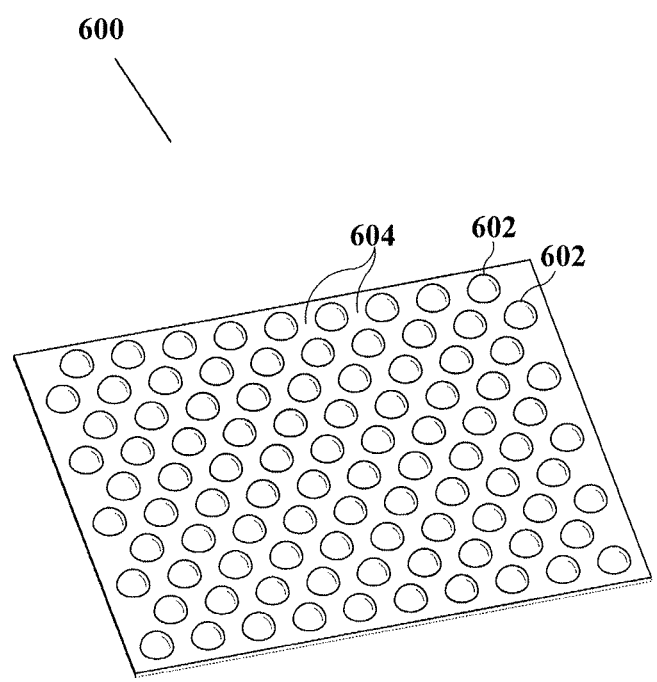
FIG. 6 is a diagram illustrating an example of a substrate having a micro-structured surface etched on a surface.

FIG. 6 is a diagram illustrating an example of a micro-structured surface 600 consistent with some embodiments. The micro-structured surface 600, sometimes also called relief structure or surface with micro-features, can have bumps 602 and valleys 604. In other embodiments, the micro-structured surface 600 can have cones, prisms, pyramids, grooves, troughs, divots and a relief pattern. In some cases, the micro-structured surface 600 can have a moth's eye structure. The micro-structured surface 600 may correspond to the micro-structured faceted proximal surface 407, the micro-structured distal surface 409, a micro-structured surface etched on a substrate, or to a micro-structured surface etched on a tool or pin, used to create the micro-structured faceted proximal surface 407 in the adhesive medium 404.

Further, consistent with some embodiments, a typical or average distance between bumps 602 may be less than 3, 1 or 0.3 times the wavelength $\lambda$ of the light used in the optical surgical probe 400. As described above, a surface without such a micro-structure can have a reflectance as high as 5%, whereas the micro-structure of surface 600 can lower the reflectance to below 1%, in some cases below 0.5%, providing a very valuable tenfold reduction in reflectance properties for thermal heat management.

The utility of this gain can be appreciated by considering that in some optical surgical probes 400 the light source can couple about 1000 mW power through the optical fiber 108 into the surgical probe 400. Without the here-described micro-structured surfaces, up to 5%, or 50 mW may be reflected back into the surgical probe 400. In some representative cases the inner diameter of the cannula 103 can be about 0.4 mm and the distance between the faceted proximal surface 107 and the end of the light guide 108 can be about 0.4 mm. Accordingly, the area of the cylindrical interior surfaces 302 to where the reflected light beams 300 and 304 are reflected into is about 0.05 mm², giving rise to a reflected power density of about $10^4$ W/m², demonstrating the seriousness and importance of the problem of managing and reducing the heat flux or flow.

The heat reflected from the faceted proximal surface 407 or the distal surface 409 can be reduced by a factor of 5, possibly up to 10 through making the corresponding surface micro-structured. This ten-fold reduction of the heat flow improves the heat and thermal management of the optical surgical probe 400 advantageously. This heat reduction can substantially reduce the likelihood of thermal degradation of the adhesive medium 404, and the possible loosening and even release of the ball lens 106.

FIGS. 7A-F are diagrams illustrating a method of manufacture and forming the optical probe 400 that has the multi-spot generator 402 with the micro-structured faceted proximal surface 407, consistent with some embodiments. The stages of the method are labeled with reference to the flowcharts of FIGS. 9A-B as well.

Figure 7A:
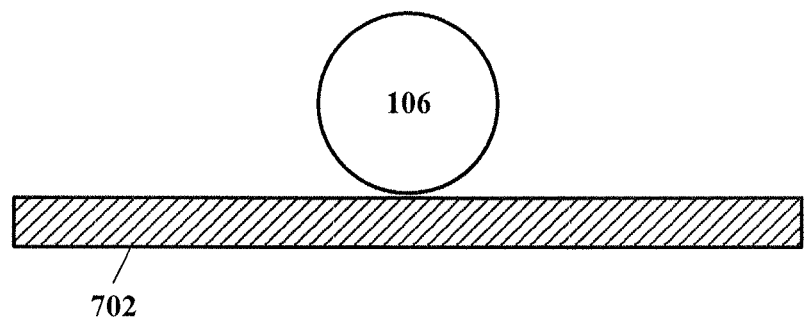
FIGS. 7A-F are diagrams illustrating forming a multi-spot generator having a micro-structured faceted proximal surface.

FIG. 7A shows that the process can be started by the step (910) placing the ball lens 106 on a substrate 702. The substrate can be, for example a quartz substrate, or another, non-adherent material.

Figure 7B:
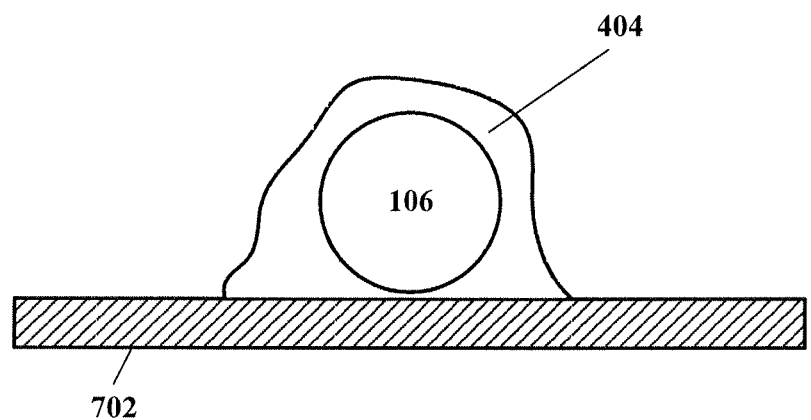
Figure 7A:
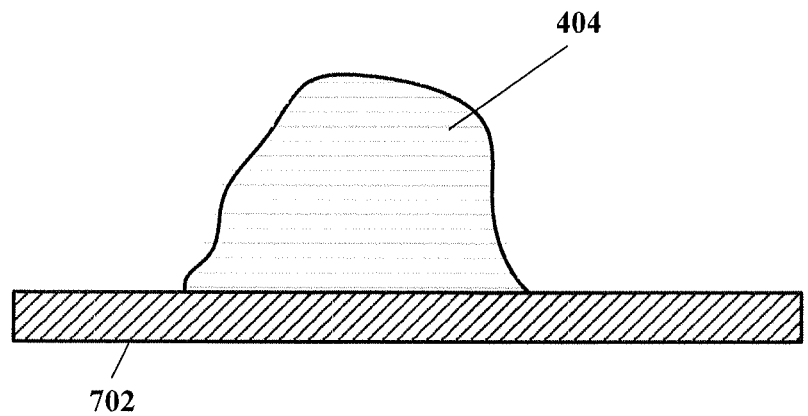
Figure 7B:
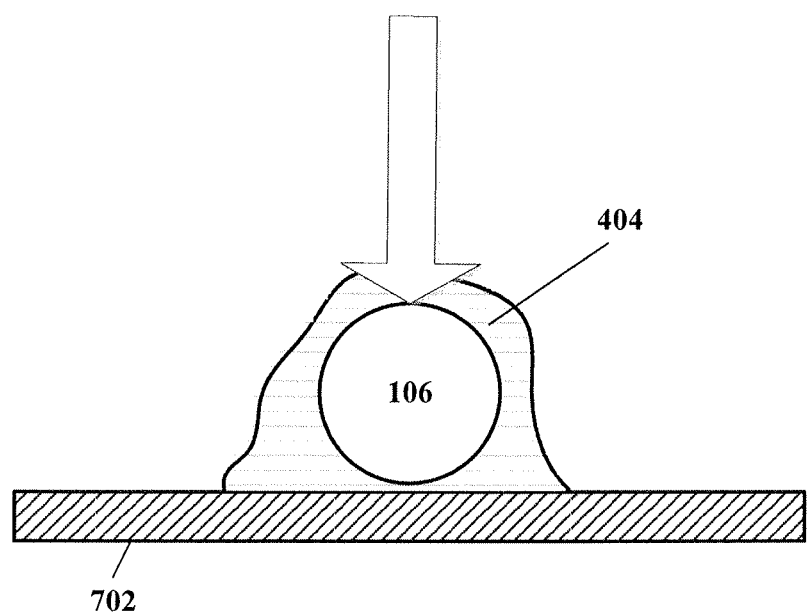

FIG. 7B shows that in the next step (920) the adhesive medium 404 can be introduced or deposited to surround and encase the ball lens 106. The adhesive medium 404 can be fluid at room temperature. In some other cases, it can be made fluid for the deposition by using an elevated temperature or a thinner or solvent.

FIGS. 7A'-B' illustrate that the steps 910 and 920 can be performed in the opposite order: first (910') the adhesive medium 404 can be deposited on the substrate 702 and then (920') the ball lens 106 inserted or disposed into the adhesive medium 404. This sequence of steps may have the following benefits: (a) the micro-structured distal surface 409 is more likely to become a continuous surface of the adhesive medium 404, uninterrupted by a protruding tip of the ball lens 106, and (b) the assembly may be easier, as when the ball lens 106 is placed on the substrate 702 first, for electrostatic or other reasons, it may roll or jump around, making precision processing difficult. Depositing the ball lens 106 into the adhesive medium 404 prevents such movements. Therefore, the 920-910 sequence may be able to offer improvements with regard to both of the above challenges.

Figure 7C:
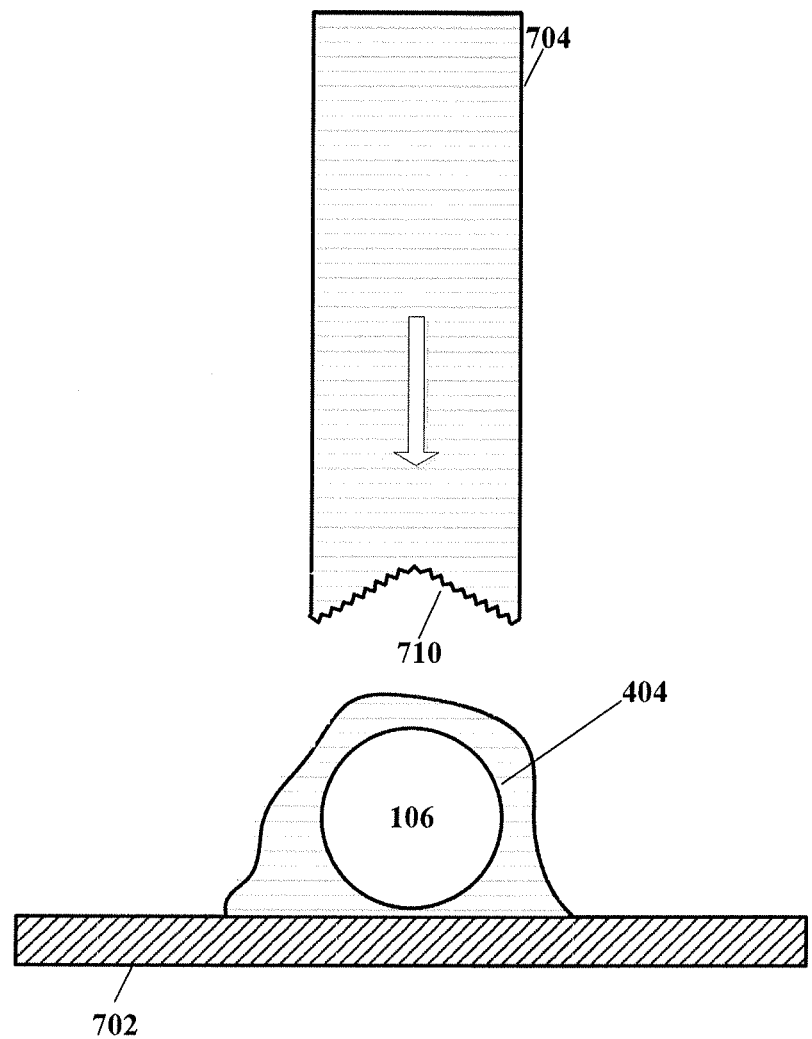
Figure 7C:
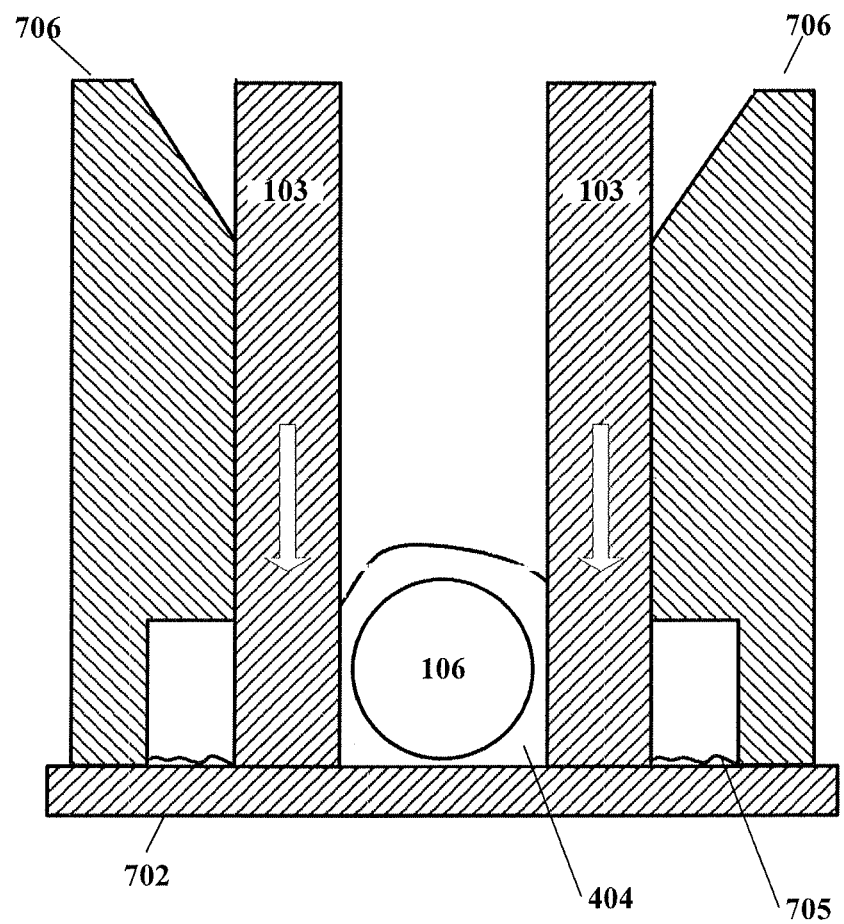

FIG. 7C shows that next in step (930) the pin 704 can be placed in contact with the adhesive medium 404. A distal end 710 of the pin 704 can be shaped as a negative of the oblique facets intended for the faceted proximal surface 407 of the multi-spot generator 402. Therefore, as the pin 704 is placed in contact with or pressed onto the adhesive medium 404 in its fluid state, the proximal surface 407 of the adhesive medium 404 assumes the oblique faceted shape described above. In addition, the faceted distal end of the pin 704 can also include a micro-structured surface 710. Upon the imprinting with the pin, this micro-structured pin surface 710 will endow the faceted proximal surface 407 with the desired micro-structure.

Figure 7D:
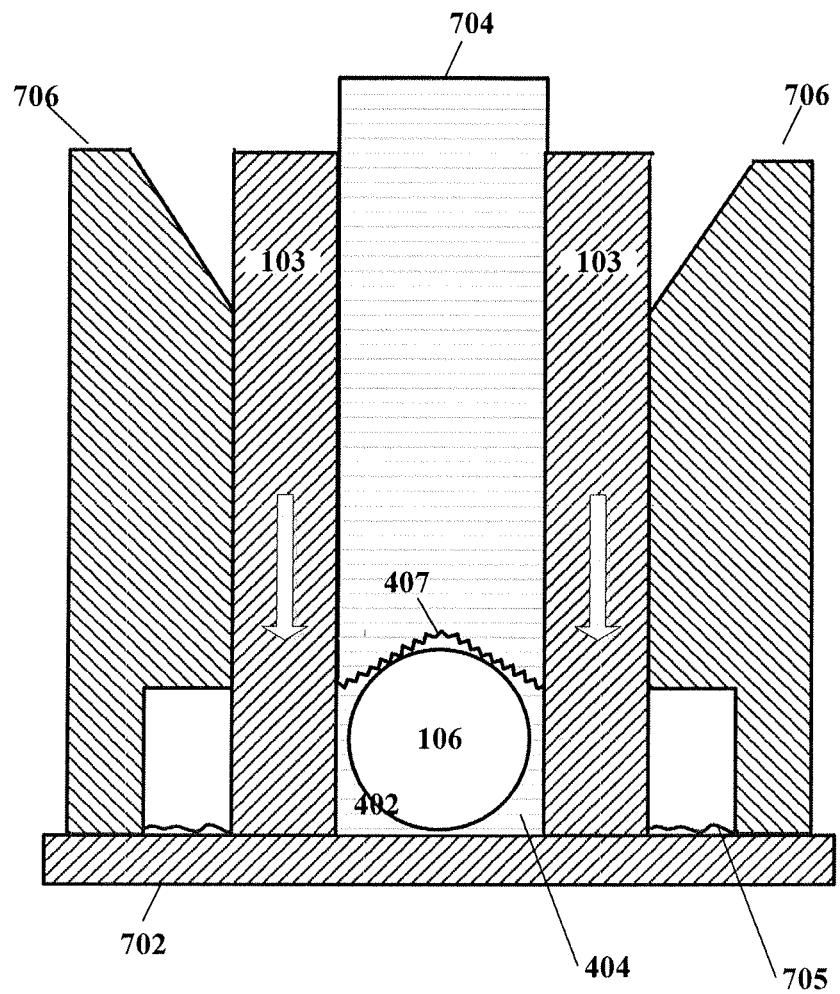
Figure 7D:
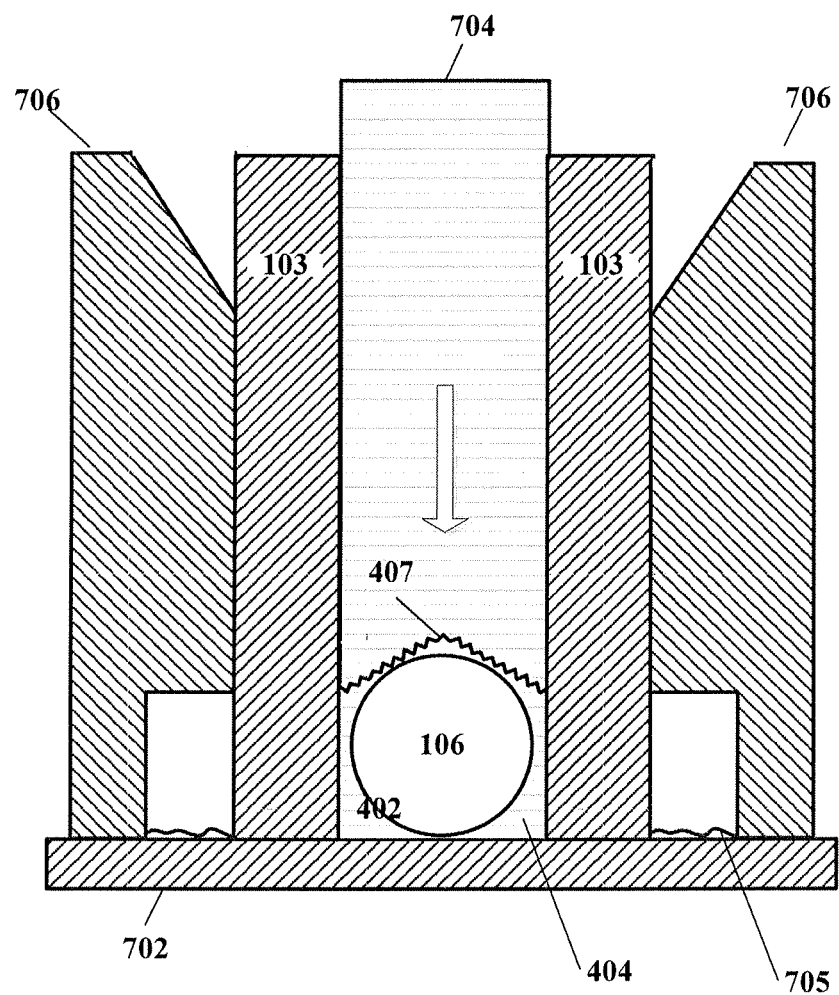

FIG. 7D illustrates that in step (940) the cannula 103 can be placed onto pin-704-adhesive medium-404-ball lens-106 structure to define the multi-spot generator 402. The cannula 103 can be guided to its place by a guide or shaft 706.

FIG. 7C' and FIG. 7D' illustrate that the steps 930 and 940 can be performed in the opposite order as well, first placing the cannula 103 on the adhesive medium 404 and then placing the pin 704 onto the adhesive medium 404.

The (930)-(940) sequence of steps allows placing the pin 704 exactly to the desired height as it permits excess adhesive 705 to flow or deform outward. In some cases, the subsequent placing of the cannula 103 can deform to some degree the top edge and side of the adhesive 404.

Performing the steps in the reverse, (940)-(930) sequence, the top edge of the adhesive medium gets filled out by the subsequent placing of the pin 704 and thus is defined well. At the same time, further adhesive 404 cannot be pushed out from the cannula 103 by the pin 704, and thus the height of the multi-spot generator 402 may be controlled only to the degree the amount of adhesive can be controlled.

Figure 7E:
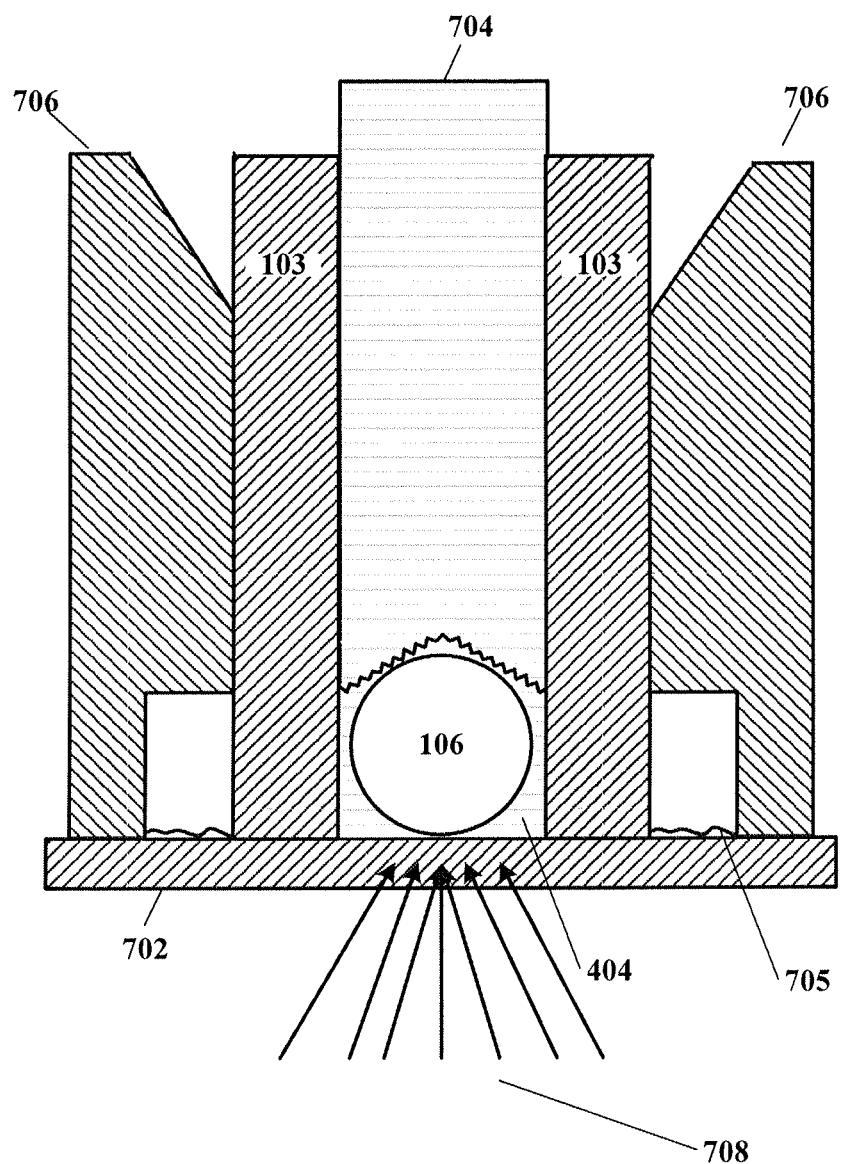

FIG. 7E illustrates that after steps 930 and 940 have been performed in either order, in step (950), the adhesive medium 404 can be cured. The curing can take place by irradiating the adhesive medium 404 with ultraviolet UV or blue light 708 through the distal surface of the substrate 702 when the substrate 702 is transparent. Curing the adhesive can make the mechanical and structural integrity of the multi-spot generator 402 more robust and well-controlled.

Figure 7F:
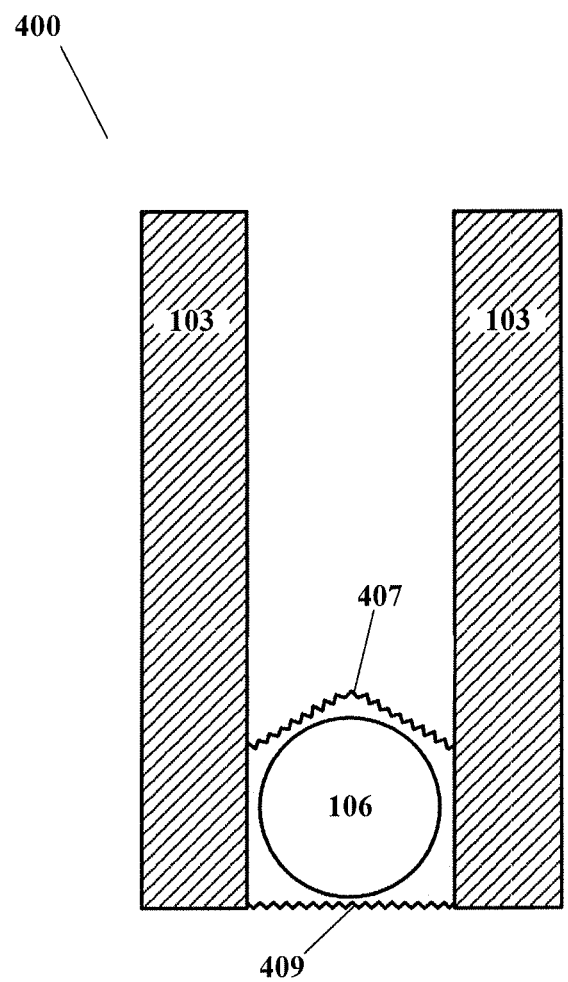

FIG. 7F shows that once the adhesive medium 404 is cured, in step (960) the pin 704 and guide 706 on one end and the substrate 702 on the opposing end may be removed to complete the optical surgical probe 400.

Next, various methods for the fabrication of the micro-structured surface 710 of the pin 704 will be described. One method is by e-beam etching the pin 704 made of hardened steel, where the individual micro-features such as bumps, pyramids, grooves and analogs of the micro-structured surface 710 are formed individually and sequentially in a scanning-type process. In other embodiments, the pin 704 can be fabricated from other type of hard materials, such as various metals, including steel, quartz, or even having a diamond head. This e-beam etching process can yield a well-articulated micro-structured surface 710 on the distal end of the pin 704. However, this direct e-beam etching method, while producing high quality pins, can be expensive and slow because e-beam etching machines are expensive and operate in a scanning manner.

Moreover, since the pin 704 is formed of a hard and thus expensive material, economic considerations favor re-using the pin 704 a large number of times. Since the pin 704 is made of a hard material, it is indeed physically possible to re-use it a number of times. However, each time the pin 704 is re-used, a small amount of residual adhesive medium material may remain stuck in the crevasses, valleys and troughs of the micro-structured surface 710. With every use, these residual deposits fill up the crevasses and valleys of the micro-structured surface 710 more and more, reducing the number of times the expensive hard-material pin 704 can be re-used. It may be also possible to periodically remove residue from the crevasses and valleys 604 by cleaning, thus slowing down the rate of residue buildup. In some cases, the cleaning may be able to return the micro-structured surface essentially into its original condition.

At least because of the just-listed problems related to cost, speed and number of re-use, another method can be also used to fabricate the micro-structured surface 710 of the pin 704. This method involves creating an intermediate tool, such as a master-tool made of a suitably hard material, such as diamond or hardened steel, and then e-beam etching a micro-structured surface onto the end surface of the master-tool. Next, a large number of "blank" pins 704 can be created from a material with hardness that is between that of the master-tool and the adhesive medium 404, such as a molded or fluid plastic. The master-tool can be used to imprint the entire micro-structured surface 710 onto the blank pins 704 during a single imprinting step instead of the sequential e-beam etching, thus creating the individual micro-features of the micro-structured surface 710 simultaneously, in parallel.

The master-tool can have a pyramid or other faceted shape machined into its end. Since the pin 704 has the negative or inverse of the faceted proximal surface 407, the master-tool can take the positive, non-inverted shape of the desired faceted proximal surface 407. Imprinting the pin 704 with the positive faceted and micro-structured end of the master-tool creates the micro-structured negative surface 710 of the pin. Since the pin 704 is harder than the adhesive medium 404, the pin 704 can be used to imprint the proximal micro-structured surface 407 on the adhesive material 404 of many multi-spot generators 402.

Therefore, a single use of the more expensive e-beam etched master-tool can lead to the creation of a large number of optical probes 400 with micro-structured surfaces 407, thus spreading the cost of the e-beam etching of a micro-structured surface over a larger number of optical probes 400.

Another intermediate-tool based method can form the micro-structured surface 710 of the pin 704 with injection molding. Here a micro-structured mold-tool can play a role analogous to that of the master-tool, having a pyramid shaped mold feature with the micro-structured surface e-beam etched into it. This intermediate mold-tool can then be used repeatedly to create a large number of pins 704 with micro-structured surfaces 710.

Both intermediate-tool processes enable the fabrication of a large number of multi-spot generators 402 with a single use of the directly e-beam etched expensive master- or mold-tools. Therefore, the rate of buildup of residue in the expensive e-beam-etched micro-structured surface per optical surgical probe 400 is slowed down, extending the effective number of uses of the intermediate tools and thus improving the economics of the fabrication process.

Some intermediate tool methods can increase the number of optical surgical probes fabricated by a single e-beam etched tool (before the residue buildup lowers the quality of the fabricated micro-structured surface below a preset threshold) by a factor of more than 10, 100, or 1,000.

Expressed in another manner, in the first, direct imprinting system that does not use intermediate tools, the number of directly e-beam-etched tools that are needed to fabricate the same number of multi-spot generators 402 can be substantially higher than in the intermediate tool methods, thus raising the cost of manufacture.

The performance of all of the above methods can be improved by forming a mold-release layer on the e-beam-etched surface of the pin 704 itself in the direct method, or on the e-beam-etched surface of the master-tool or mold-tool in the corresponding intermediate-tool methods. The mold-release layer can be as thin as a single atom or few-atom layers. Its chemical composition can be chosen such that it does not "wet" the micro-structured surface, or in other words, does not adhere to it. Introducing such a mold-release layer can further reduce the buildup of residues in the micro-structured e-beam-etched surface to a considerable degree.

Figure 8:
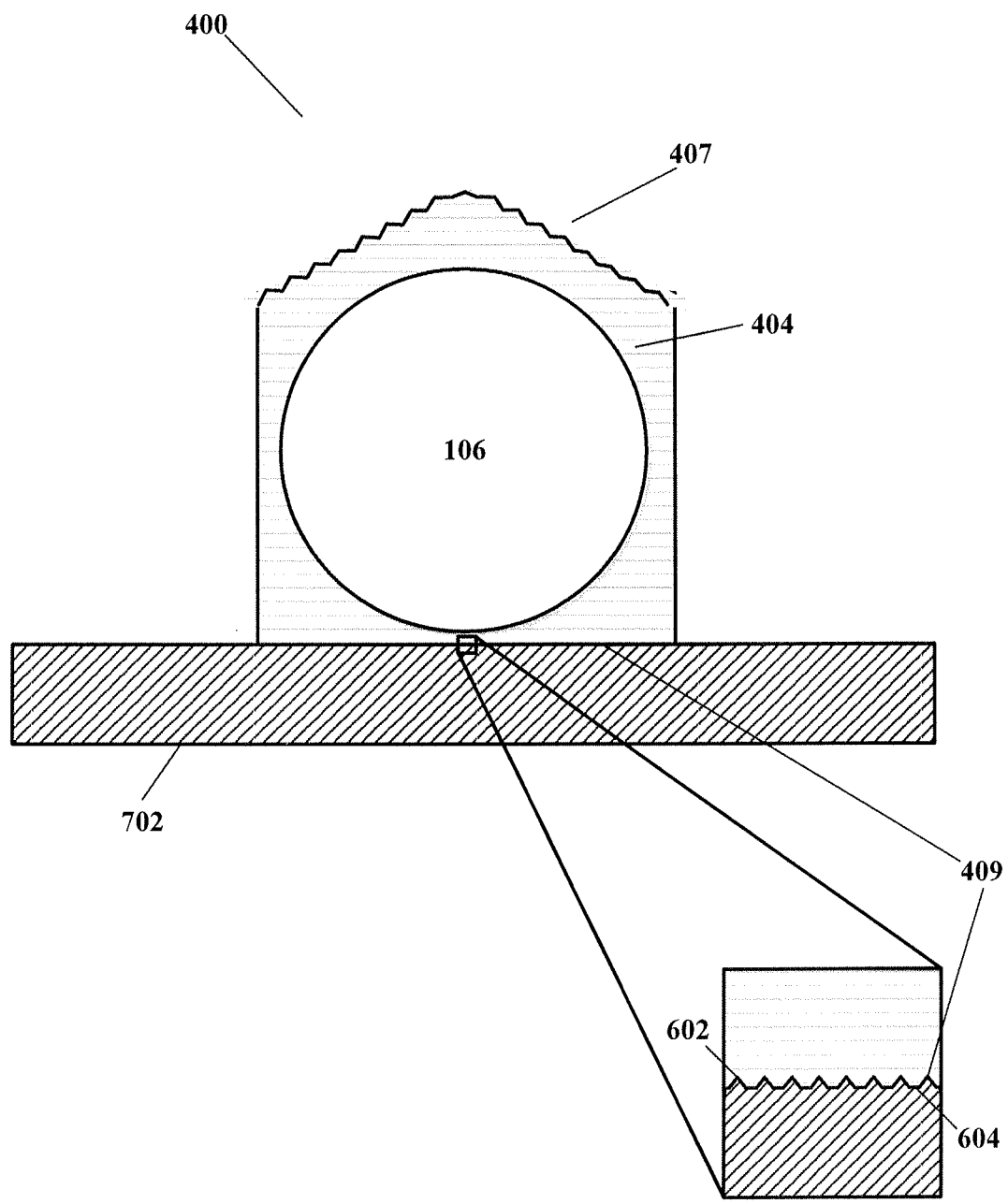
FIG. 8 is a diagram of an optical surgical probe with a micro-structured distal surface.

FIG. 8 illustrates that in some embodiments, a micro-structured surface can be also formed on the distal surface 409 of the multi-spot generator 402. Implementing such micro-structured surfaces on both ends of the multi-spot generator 402 can reduce the overall reflected light very efficiently. As discussed earlier, implementing a micro-structured surface on the proximal surface 407 or the distal surface 409 of the multi-spot generator 402 can reduce the reflectivity of that surface from a value of up to 5% to below 0.5%.

Consistent with some embodiments, substrate 702 may be a quartz plate having a micro-structured surface etched into a proximal surface thereof, for example, by e-beam etching. The micro-structured surface can have bumps 602 and valleys 604. These micro-features can be separated by a typical distance that is less than 3, 1, or 0.3 times the wavelength $\lambda$, of the light used by the optical surgical probe 400.

Consistent with some embodiments, the micro-structured surface of the substrate 702 may be formed directly by e-beam etching, or by using an intermediate tool that itself was formed by e-beam etching. The intermediate tool can be an imprinting tool or master tool, analogous to the above-described intermediate tools. If the substrate 702 is harder, such as quartz, then the imprinting tool can be also harder, such as hardened steel. Using such intermediate tools can again improve the economy of the manufacture process because of the re-use of the expensively etched surface.

The micro-structured surface of the substrate 702 gets utilized during step 920, illustrated in FIG. 7B, when the adhesive 404 is deposited on the substrate 702. Because of its malleability, the adhesive medium 404 will form the distal surface 409 with the desired micro-structure. The curing step 950, illustrated in FIG. 7E then solidifies the micro-structured distal surface 409.

As before, the substrate 702 with the micro-structured surface can be re-used repeatedly to form a large number of distal surfaces 409 of the multi-spot generator 402. This re-use is a further improvement of the economy of the manufacturing process.

As before, to assist the re-use of the micro-structured substrate and micro-structured intermediate tool, consistent with some embodiments, a mold release layer can be formed on the micro-structured surface of the substrate or the tool. This mold-release layer reduces the amount of residue left behind after each imprinting process.

Figure 9A:
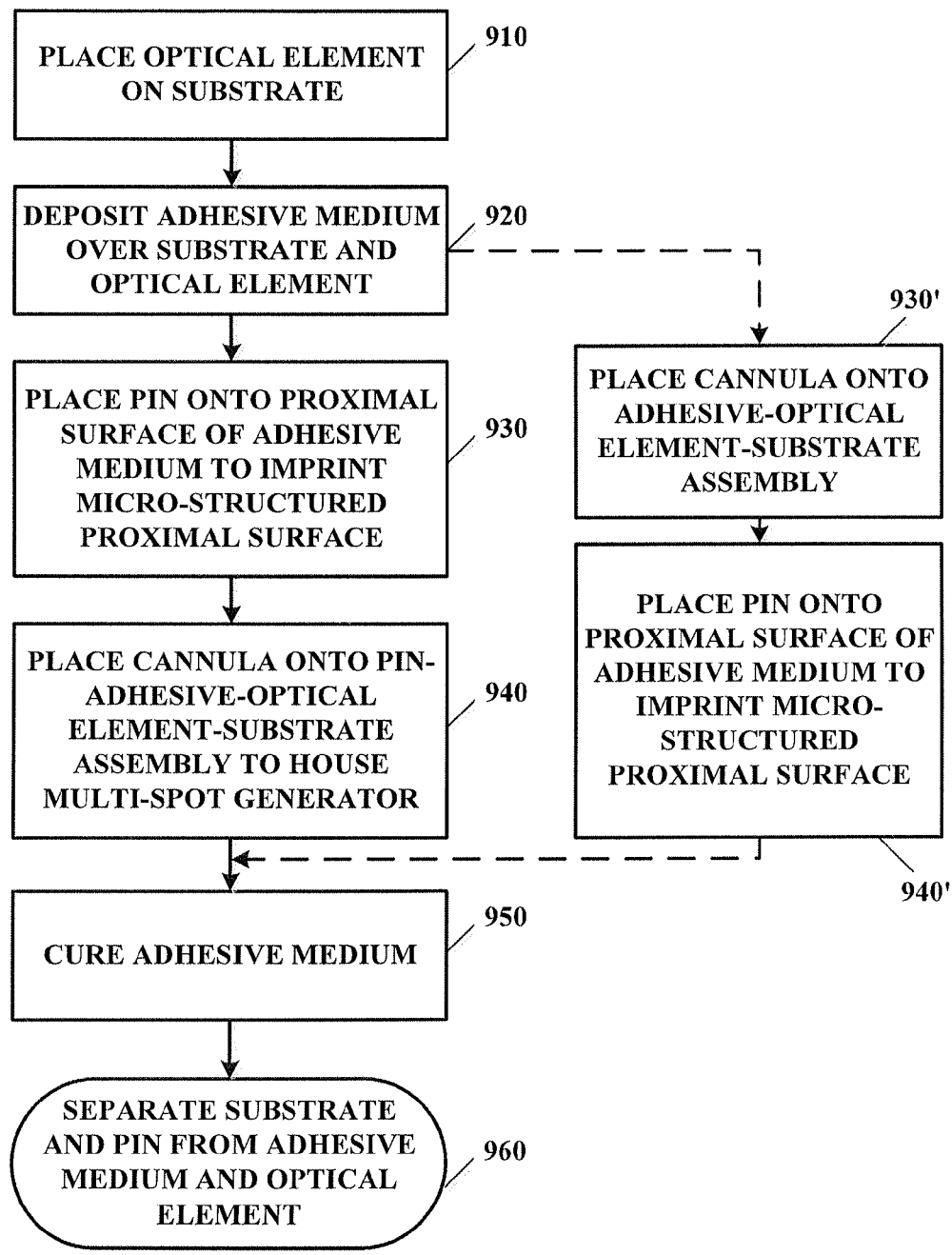
FIGS. 9A-B are flowcharts illustrating a method for manufacturing a multi-spot generator a micro-structured distal surface and a micro-structured faceted proximal surface.

FIG. 9A is a flowchart illustrating a method for manufacturing a multi-spot generator, consistent with some embodiments. For the purpose of illustration, FIG. 9A may be described with reference to any of FIGS. 1-8.

Step 910 can include placing an optical element such as the ball lens 106 on a substrate 702. The substrate can be, for example a quartz substrate, or another, non-adherent material.

Step 920 can include introducing the adhesive medium 404 to surround and encase the ball lens 106. The adhesive medium 404 can be made fluid for the deposition by using an elevated temperature or a thinner or solvent. Or it can be already fluid or viscous at room temperature. The refractive index of the adhesive can be in the range of 1.5-1.6, in some cases in the range of 1.56-1.58.

Figure 9B:
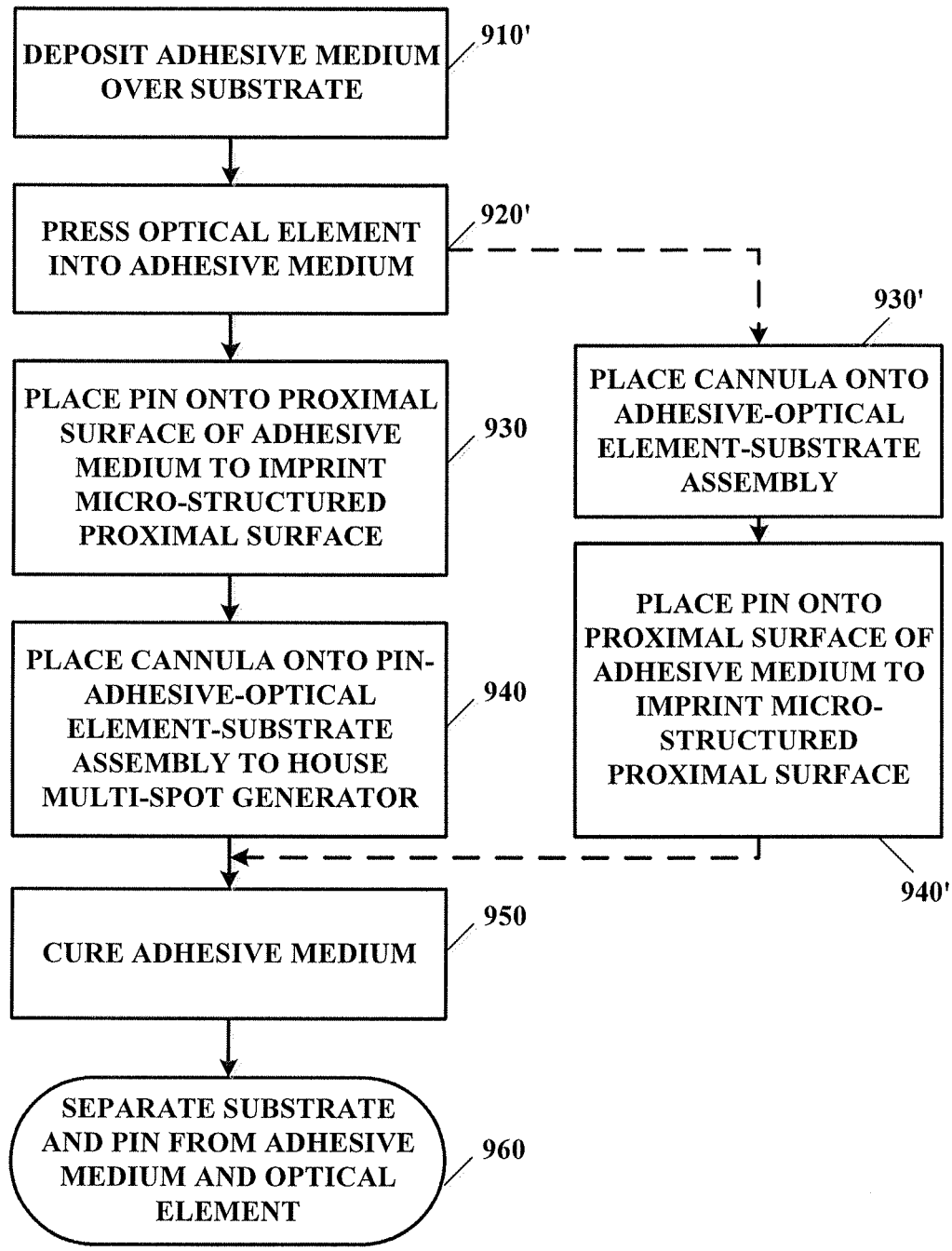

FIG. 9B illustrates that steps 910 and 920 can be performed in reverse order, first (910') introducing the adhesive 404 and then (920') inserting the optical element 106 into the optical adhesive 404. This sequence may form a higher quality distal surface for the optical surgical probe 400, and can reduce or eliminate an uncontrolled movement or rolling of the ball lens 106 during fabrication, as discussed in relation to FIGS. 7A'-B'.

Step 930 can include pressing or placing the pin 704 onto the adhesive medium 404. A distal end 710 of the pin 704 can be shaped as a negative of the oblique facets intended for the faceted proximal surface 407 of the multi-spot generator 402. Therefore, as the pin 704 is placed in contact with or pressed onto the fluid adhesive medium 404, the proximal surface 407 of the adhesive medium 404 assumes the oblique faceted shape described above.

In addition, the faceted distal end of the pin 704 can also include the micro-structured surface 710. Upon the imprinting with the pin 704, this micro-structured pin surface 710 will endow the faceted proximal surface 407 with the desired micro-structure. A modulation length of the micro-structured surface can be less than 3, 1, or 0.3 times a wavelength λ, of the laser beam used by the optical surgical probe. The micro-structured surface 710 can include a mold-release layer to reduce the amount of residue of the adhesive surface sticking to the micro-features of the micro-structured surface. The less residue sticks to the micro-structured surface 710, the more the pin 704 can be re-used.

Step 940 can include pressing or placing the cannula 103 onto the pin-704-adhesive medium-404-ball lens-106-substrate 702 structure to house the multi-spot generator 402. The cannula 103 can be guided to its place by a guide or shaft 706.

The steps 930 and 940 can be performed in the opposite order (940)-(930) as well, first pressing or placing the cannula 103 onto the adhesive medium 404 and then pressing or pacing the pin 704 onto the adhesive medium 404. Both orders have advantages and disadvantages, as described above.

Step 950 can include curing the adhesive medium 404. The curing can take place by irradiating the adhesive medium 404 with ultraviolet UV or blue light 708 through the distal surface of the substrate 702 when the substrate 702 is transparent. Curing the adhesive can make the mechanical and structural integrity of the multi-spot generator 402 more robust and well-controlled.

Step 960 can include separating the pin 704 and guide 706 on one end and the substrate 702 on the opposing end to complete the optical surgical probe 400.

Embodiments as described herein may provide a multi-spot laser probe having a micro-structured distal surface and a micro-structured faceted optical element and a method for manufacturing the same that may reduce an internal reflectance within the laser probe. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An optical surgical probe comprising:
   a cylindrical cannula;
   a light guide within the cannula, the light guide configured to receive a light beam from a light source, to guide the light beam to a distal end of the light guide, and to emit the light beam at the distal end of the light guide; and
   a multi-spot generator at a distal end of the cannula, the multi-spot generator having a faceted proximal surface with oblique facets, configured to receive the light beam emitted at the distal end of the light guide and to split the received light beam into multiple beam-components, an a distal surface through which the multiple beam-components exit the multi-spot generator, wherein the proximal surface of the multi-spot generator is micro-structured with a modulation length smaller than a wavelength of the light beam.

2. The probe of claim 1, the proximal surface of the multi-spot generator comprising:
   micro-structures, with an average separation less than the wavelength of the light beam.

3. The probe of claim 2, the micro-structures comprising at least one of: bumps, cones, prisms, pyramids, grooves, troughs, divots and a relief pattern.

4. The probe according to claim 1, wherein: the proximal surface of the multi-spot generator has a moth's eye structure.

5. The probe according to claim 1, wherein: the proximal surface of the multi-spot generator is micro-structured to have an effective index of refraction that reduces a reflection of the light beam by the proximal surface of the multi-spot generator to below 1%.

6. The probe of claim 1, the multi-spot generator comprising:
   a cured adhesive medium at a distal end of the cannula, the micro-structured proximal surface being formed at a proximal surface of the adhesive medium; and
   a ball lens, disposed in the cured adhesive medium.

7. The probe of claim 6, the ball lens comprising:
   a sapphire ball lens.

8. The probe of claim 1, the multi-spot generator comprising:
   a distal surface, micro-structured with a modulation length smaller than the wavelength of the light beam; and the proximal surface and the distal surface of the multi-spot generator are micro-structured to have effective indices of refraction that reduce an overall reflection of the light beam by the multi-spot generator to below 1%.

\* \* \* \* \*